United States Patent [19]

Sabbatini

[11] 4,143,229

[45] Mar. 6, 1979

[54] PROCESS FOR THE PREPARATION OF PARA-SUBSTITUTED DERIVATIVES OF ALPHA-PHENYLPROPIONIC ACID

[75] Inventor: Massimo Sabbatini, Milan, Italy

[73] Assignee: Alcar S.R.L., Milan, Italy

[21] Appl. No.: 790,549

[22] Filed: Apr. 25, 1977

[30] Foreign Application Priority Data

Apr. 23, 1976 [IT] Italy ................. 22610 A/76

[51] Int. Cl.$^2$ ............................................. C07C 63/52
[52] U.S. Cl. ........................... 562/496; 260/566 A; 260/599; 568/592
[58] Field of Search ................... 260/515 R

[56] References Cited

U.S. PATENT DOCUMENTS

| | | | |
|---|---|---|---|
| 3,457,300 | 7/1969 | Dorn et al. | 260/515 R |
| 3,825,572 | 7/1974 | van Venrooy et al. | 260/599 |
| 3,965,161 | 6/1976 | Kogure et al. | 260/515 |
| 4,052,194 | 10/1977 | Wilcox | 260/566 A |

OTHER PUBLICATIONS

Heldt et al., Organic Reactions II, pp. 1–156 (1960).
Patai, *The Chemistry of the Carbon–Nitrogen Double Bond*, pp. 408–439 (1970).
Jordan et al., J.A.C.S. 58, pp. 1304–1305 (1936).
Fieser et al., Reagents for Organic Synthesis, vol. I, pp. 479, 1204, 1205 (1967).
Brewster et al., Organic Chemistry, Third Edition, pp. 760–761 and 179, (1964).

*Primary Examiner*—Jane S. Myers
*Attorney, Agent, or Firm*—Joseph W. Molasky

[57] ABSTRACT

Pharmacologically useful alpha (para-alkylphenyl) propionic acids having anti-inflammatory, analgesic and antipyretic activity are prepared from the corresponding 1-haloethyl-para-alkylbenzene by converting same to a diethylacetal via a Grignard reaction, followed by the conversion of said acetal to the corresponding aldehyde by hydrolytic means, converting the said aldehyde to an oxime derivative and hydrolyzing the latter to the desired acid.

6 Claims, No Drawings

1

PROCESS FOR THE PREPARATION OF PARA-SUBSTITUTED DERIVATIVES OF ALPHA-PHENYLPROPIONIC ACID

BACKGROUND OF THE INVENTION

Para substituted alpha-phenylpropionic acids are known to have anti-inflammatory, analgesic and antipyretic properties comparable or superior to those of aspirin, which properties make these compounds particularly useful in the treatment of rheumatoid arthritis.

The compound Ibuprofen, or 2-(4-isobutylphenyl) propionic acid, has gained wide acceptance as a therapeutic agent for the treatment of rheumatoid arthritis to relieve pain, reduce fever, swelling and tenderness. These compounds and their uses are described for example in British Pat. No. 971,700 and corresponding U.S. Pat. Nos. 3,228,831 and 3,385,886 and in Adams et al. Arch. Pharmacodyn. Ther. 178: page 115 (1969), the disclosures of which are incorporated by reference. The foregoing disclosures also set out several processes for the preparation of para substituted, alpha-phenylpropionic acids, which processes are, for the most part, more theoretical than practical and do not lend themselves readily to satisfactory industrial application.

It is, therefore, an object of this invention to provide a novel synthetic route for the preparation of para substituted alpha-phenylpropionic acids which is especially well suited to manufacturing such compounds on an industrial scale and, in particular, a process for manufacturing 2-(4-isobutylphenyl)propionic acid and its pharmaceutically useful salts and derivatives.

BRIEF SUMMARY OF THE INVENTION

This invention provides a novel process for the preparation of para substituted alpha-phenyl propionic acids particularly the pharmaceutically useful 2-(4-lower alkylphenyl)propionic acids which readily lends itself to the commercial production of pharmaceutically acceptable products. The novel process of this invention is shown schematically as follows:

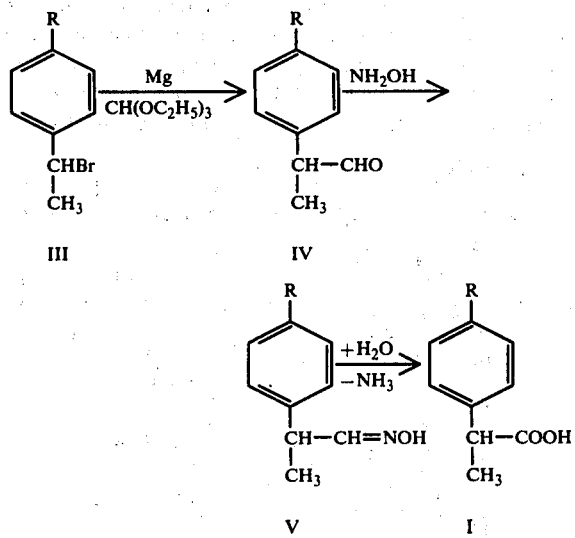

wherein R is lower alkyl of 1 to 6 carbon atoms.

Thus, the process of this invention provides a commercially adaptable method for preparing 2-(4-lower alkylphenyl)propionic acids from the corresponding 1-halo ethyl-para-loweralkylbenzene, which latter compounds are readily available starting materials easily prepared in an industrially economical way in high yields. The overall novel process comprises the three principal reactions shown above, each of which is in itself a novel process.

DETAILED DESCRIPTION OF THE INVENTION

In accordance with this invention it has now been found that para-substituted, alpha phenylpropionic acids of the formula:

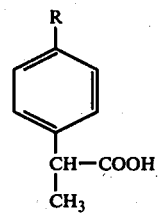

wherein R is lower alkyl of 1 to 6 carbon atoms and includes branched and straight chain lower alkyl such as methyl, ethyl, propyl, isopropyl, butyl, isobutyl, sec-butyl, tert-butyl, pentyl, isopentyl, hexyl and the like, can be prepared by the following sequence of novel reaction steps. In this description reference is made to specific starting materials and intermediates, such as the 1-(para-lower-alkylphenyl)1-bromoethane reactant (III, infra); however, it is to be understood that this is for illustration purposes only and, in practice, other functionally equivalent derivatives may be substituted therefor.

The 1-(4-lower-alkylphenyl)propionic aldehyde derivative (IV) is prepared according to the following reaction:

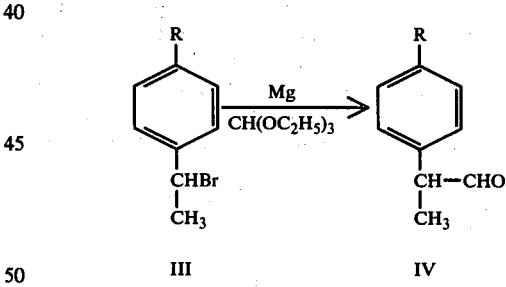

wherein R is as defined above.

In this step the 1-(para-lower alkylphenyl)1-bromoethane (III) is treated with powdered magnesium. The reaction is carried out in a suitable organic solvent, preferably, anhydrous ethyl ether at a temperature in the range of from about 20° C. to about 60° C. and, preferably, at ambient or room temperature. Preferably, this reaction is conducted by adding the bromide dropwise or diluted with solvent to a mixture of the Grignard reagent, and a trace of iodine in the reaction solvent. The reaction mixture can be heated to assure complete formation of the magnesium bromide compound. The magnesium bromide compound thus formed is then treated with ethyl formate or, optionally, with orthoethyl formate, to produce the diethyl acetal of the formula:

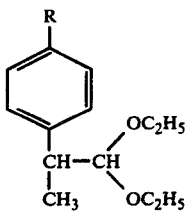

wherein R is as defined above.

The diethylacetal of formula (IVa) is then hydrolyzed with a solution of strong acid to afford the corresponding aldehyde (IV).

The reaction with ethyl formate or ortho-ethyl formate is carried out in the presence of in inert organic solvent, at a temperature of between about 0° C. and 40° C. Any inert organic solvent can be used although, preferably, it is the same solvent as used in the preceeding reaction with magnesium, that is, anhydrous ethyl ether. The hydrolysis is carried out by adding an aqueous solution of a strong mineral acid, such as HCl or $H_2SO_4$, to the diethylacetal compound after removal of the solvent. This is accomplished, for example, by evaporation at a temperature between about 0° C. and about 60° C. The aldehyde intermediate (IV) thus obtained is then separated from the hydrolysis reaction mixture, washed and converted to the corresponding oxime as shown below. The separation can be conveniently effected by any of the usual techniques such as steam distillation.

It is important to note that the reaction by which the bromide intermediate (III) is converted to the corresponding aldehyde (IV) does not involve separation of the intermediate compounds, but is carried out in sequence, in one operation. In any event, however, the indicated operations for the preparation of the aldehyde (IV) are brought to completion by formation of the aldehyde, purification, generally, by steam distillation and precipitation of the corresponding Bertagnini compound. The reaction time is generally several hours but will depend in each case upon the starting material, the reaction medium, and the selected reaction temperature.

The oxime of the aldehyde of formula (IV) is prepared according to the following reaction:

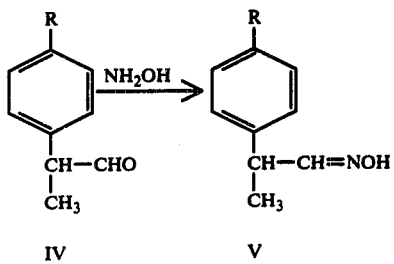

wherein R is as defined above. This step is carried out by treating the aldehyde dissolved in an organic solvent with hydroxylamine hydrochloride and neutralizing the reaction mixture with a suitable base.

The reaction between the aldehyde and the hydroxylamine is preferably carried out by adding the hydroxylamine to the aldehyde dissolved in an inert organic solvent or by adding an aqueous solution of hydroxylamine hydrochloride to the solution of the aldehyde in an inert organic solvent.

The organic solvent may be any of the usual solvents such as methanol, ethanol, tetrahydrofuran, pyridine, and the like. The reaction temperature is preferably kept around room temperature, but in any case it is kept between about 20° C. and about 100° C. The base used for neutralizing the reaction mixture is preferably an aqueous solution of an alkaline hydrate such as KOH or NaOH. The 2(4-lower alkylphenyl) propionoxime intermediate prepared in this way can be used directly for conversion to the 2-(4-lower alkylphenyl) propionic acid or, if desired, it can be separated from the solvent, washed and then used as an intermediate in the preparation of 2-(4-lower alkylphenyl) propionic acid (I).

The 2-(4-lower alkylphenyl) propionic acid (I) is obtained from the corresponding oxime (V) by hydrolysis and deammoniation as defined by the following reaction sequence:

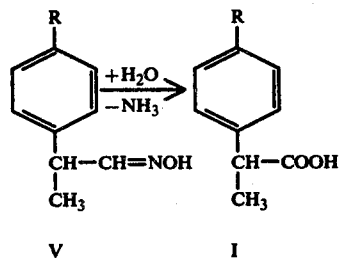

wherein R is as defined above.

In conducting this step it is not necessary to purify the oxime (V) before subjecting it to the hydrolysis reaction, and the reaction mixture may be used as such. In any case the hydrolysis-deammoniation step is carried out in an aqueous medium in the presence of either a strong alkali or a strong acid by adding the oxime or the oxime reaction product to an aqueous solution of the alkali or acid and heating at a temperature between about 100° C. and about 200° C. in a nitrogen atmosphere and maintaining the temperature until the formation of ammonia has ceased.

Any strong alkali may be used though the preferred alkalies are KOH and NaOH; the preferred acids are the mineral acids such as HCl and $H_2SO_4$.

The reaction time can be varied within a large range depending on the specific oxime being treated. The acid is easily recovered by extracting from the aqueous solution with an organic solvent from which it readily is crystallized. Any of the usual organic solvents can be used to extract the acid from the aqueous solution though carbon tetrachloride is preferred.

The reactants and the reaction conditions of the previous steps do not present any difficulty in industrial execution.

As mentioned previously, the starting product 1-(para-lower-alkylphenyl)-1-bromethane may be prepared in several ways. The preferred process in the practice of this invention comprises the following steps.

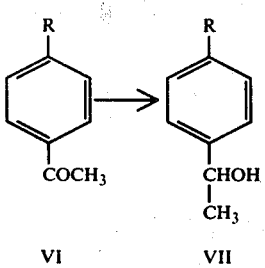

wherein R is as defined above.

This reduction is preferably carried out with aluminum isopropylate in anhydrous isopropyl alcohol. The acetone so formed is extracted by distillation and the heating is stopped only when acetone is no longer recovered.

The bromination is carried out with HBr, refluxing in the presence of concentrated sulphuric acid and ethanol for about 2 to 3 hours.

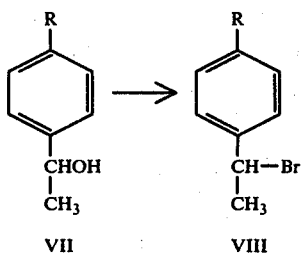

wherein R is as defined above.

The operational details and the yields obtained in each step of the above mentioned process will become evident from the following examples which refer to the preparation of the most interesting compound among those included in the formula (I), that is to the preparation of 2-(4-isobutylphenyl) propionic acid of the formula:

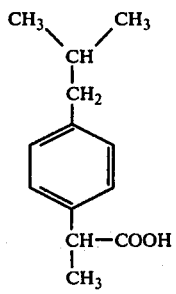

II

It is evident that the methods of operation may vary depending on the compound which is to be prepared and that for the same compound better results also may be obtained by modifying the conditions of solvents, temperatures and time. In any case it is clear that such modifications are included in the scope of the present invention. Where, as in the case of formula II, the compounds can exist as optically active isomers, it is intended to include the preparation of such isomers and mixtures thereof.

The following examples are by way of illustrating a specific embodiment of the invention and are not to be construed as a limitation thereon.

SPECIFIC EMBODIMENTS
EXAMPLE 1

1-(Para-isobutyl phenyl)-1-bromoethane.

Finely ground aluminum isopropylate (20.0 g.), 100 ml of anhydrous propanol and 17.4 g. (0.099 moles) of para-isobutyl-acetophenone is introduced into a 250 ml flask. The flask is connected to a distilling apparatus and the reaction mixture heated until elimination of the acetone which has formed is complete. Then the reaction mixture is diluted with isopropyl alcohol, the excess of alcohol is eliminated under vacuum and the excess of aluminum isopropylate destroyed by the addition of aqueous HCl while stirring vigorously and cooling.

The 1-(para-(isobutyl phenyl) ethanol so formed is separated by steam distillation, dried on $MgSO_4$ and vacuum distilled.

Pure 1-(para-isobutylphenyl) ethanol is obtained (boiling point 110°–120° C. at 2 mm Hg) with a yield of 85–90%.

HBr (250.0 g.) at 48% is introduced into a 3 necked 500 ml flask equipped with a reflux condenser, mechanical stirrer and a dropping funnel. Then 75 g (41 ml) of concentrated sulphuric acid is added while stirring.

1-(para-isobutylphenyl) ethanol (213.6 g.; 1.2 moles) prepared as above, is introduced slowly into the flask, followed by 60 g (32.5 ml) of concentrated sulphuric acid. The mixture is refluxed for 2 to 3 hours followed by steam distilling the reaction mixture to produce 5 to 6 liters of distillate, which is then extracted with about 1 liter of benzene.

The organic solution is washed 2 and 3 times with water, then with aqueous NaOH (5–10%) and finally dried on $MgSO_4$.

After solvent evaporation 1-(para-isobutyl phenyl)-1-bromoethane is obtained, having a B.P. of 130°–140° C. at 2 mm Hg. Yield 88–92%.

EXAMPLE 2

Alpha-para-isobutyl-phenyl propionic aldehyde.

Grignard magnesium (15.0 g.) and 25–30 ml of anhydrous ethyl ether are introduced into a 3 necked flask equipped with a mechanical stirrer, reflux condenser and a dropping funnel. Then a small crystal of iodine and 0.025 moles of 1-(para-isobutyl phenyl)-1-bromo ethane is added.

As soon as the reaction begins, 100 ml of anhydrous ether is added into the flask and then while stirring, drop by drop, a solution of 0.6 moles of bromide dissolved in about 100–150 ml of anhydrous ether is also added.

The reaction mixture is refluxed for about half an hour after the end of the bromide addition and is then cooled to about 5° C. Then 74 g. (83 ml) of ethyl-orthoformate is added and the mixture refluxed for about 6 hours. After refluxing the excess ehtyl ether is evaporated and the cooled residue is added, while stirring, to 375 ml of 6% HCl, previously cooled with ice. When all the white solid is dissolved, the organic layer consisting mainly of the aldehyde diacetal, is separated and hydrolyzed by heating under nitrogen with a solution of 27.5 ml of concentrated sulphuric acid in 350 ml of water.

The aldehyde is separated by steam distillation and purified by rinsing with a solution of 70 g. of $NaHSO_3$ in 150 ml of cold water.

EXAMPLE 3

Oxime of the alpha-(para-isobutyl phenyl) propionic aldehyde.

The alpha-(para-isobutylphenyl) propionic aldehyde (380.0 g.) prepared in accordance with Example 2 above is dissolved in 500 ml of ethanol and added while stirring to 175 g. of NH$_2$OH.HCl at room temperature. When the addition is complete aqueous NaOH is added to neutralize the HCl formed. The oxime separates as an oily liquid which is washed with slightly acid water containing a small quantity of CaCl$_2$. Yield 98%.

EXAMPLE 4

Alpha-(para-isobutyl phenyl) propionic acid.

The oxime of the alpha-(para-isobutyl phenyl) propionic aldehyde (100.0 g.) prepared in accordance with Example 3 is suspended in 50 ml of water containing 50 g. of KOH at 90%. The mixture is heated in a nitrogen atmosphere at 115°-120° C., until the formation of ammonia stops. Then the reaction mixture is diluted with 500 ml of water, extracted four times with 50 ml of CCl$_4$ and eventually boiled and acidified. After cooling the acid separates as a crystalline produce which is recrystallized with N-heptane (M.P. 74°-76° C. Yield 75-77%).

By analogous methods using other 1-(para-lower alkylphenyl)-1-bromoethanes the other corresponding alpha (para-lower alkyl substituted phenyl)propionic acids (I) can also be prepared.

It will be apparent from the foregoing description that the products of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A process for the preparation of para-substituted derivatives of alpha-phenyl propionic acids of the formula:

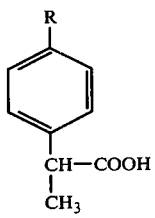

wherein R is lower alkyl of 1 to 6 carbon atoms, which comprises treating an oxime of the formula:

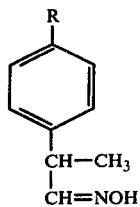

wherein R has the same meaning as above at a temperature of between about 100° C.-200° C. in an aqueous medium with an hydrolysing agent selected from the group consisting of strong alkalis and strong acids, until the elimination of ammonia is complete.

2. The process of claim 1, wherein the hydrolysing agent is concentrated KOH.

3. The process of claim 1, wherein the reaction is carried out at a temperature between about 110° C. and about 130° C.

4. The process of claim 1 wherein the reaction is carried out at a temperature between about 115°-120° C.

5. A process for the preparation of alpha-phenyl propionic acid derivatives of the formula:

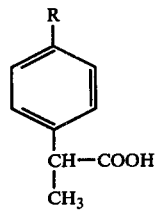

wherein R is a straight or branched chain lower alkyl of 1 to 6 carbon atoms, which comprises treating a bromide of the formula:

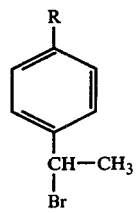

wherein R is as defined above, with powdered magnesium and then with a member selected from the group consisting of ethyl formate and ethyl-ortho formate followed by reaction with a hydrolyzing agent to afford an aldehyde of the formula:

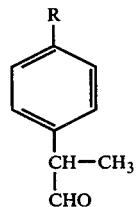

wherein R is as defined above; treating said aldehyde with hydroxylamine to give an oxime of the formula:

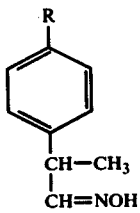

wherein R is as defined above; then treating said oxime in an aqueous medium, in the presence of a member selected from the group consisting of a strong alkali and a strong acid, at a temperature between about 100° C. and about 200° C. until the elimination of ammonia is complete to give the desired propionic acid.

6. The process of claim 5 wherein the bromide employed is 1-(para-isobutylphenyl)-1-bromoethane, the aldehyde is 2-(para-isobutylphenyl)propionaldehyde, and; the oxime is 2-(para-isobutylphenyl)propionoxime.

* * * * *